US00PP29975P2

(12) United States Plant Patent
Van Swieten

(10) Patent No.: US PP29,975 P2
(45) Date of Patent: Dec. 11, 2018

(54) ***PHALAENOPSIS* ORCHID PLANT NAMED 'PHALGULFQ'**

(50) Latin Name: ***Phalaenopsis* hybrid**
Varietal Denomination: PHALGULFQ

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/732,060

(22) Filed: Sep. 11, 2017

(51) Int. Cl.
*A01H 5/02* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALGULFQ', particularly characterized by having large, white flowers with red-purple flecks and stripes on the edge, 1 to 3 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALGULFQ'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGULFQ'.

The new *Phalaenopsis* plant is a product of a planned breeding program conducted by the inventor in Bleiswijk, The Netherlands. The objective of this breeding program was to create a new *Phalaenopsis* plant with attractive large, white flowers with red-purple flecks and stripes on the edge, suitable for potted plant production.

The new *Phalaenopsis* plant 'PHALGULFQ' is a result of cross-pollination made by the inventor in September 2008 in Bleiswijk, The Netherlands of the proprietary female, or seed parent, *Phalaenopsis* hybrid '01-6226' (unpatented) with the proprietary male, or pollen parent, *Phalaenopsis* hybrid '01-6227' (unpatented).

The new *Phalaenopsis* was selected by the inventor as a single plant within the progeny of the stated cross-pollination in a controlled greenhouse in Bleiswijk, The Netherlands in September 2011. Asexual reproduction of the new *Phalaenopsis* plant by meristem tissue culture since 2014 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 13, 2016. 'PHALGULFQ' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALGULFQ' as a new and distinct variety of *Phalaenopsis* plant.

1) Large, white flowers with red-purple flecks and stripes on the edge;
2) 1 to 3 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in July 2017. Colors in the photographs may differ from the color values cited in the detailed botanical description, which accurately describe the actual colors of the new variety.

DESCRIPTION OF THE NEW VARIETY

Figure 1:
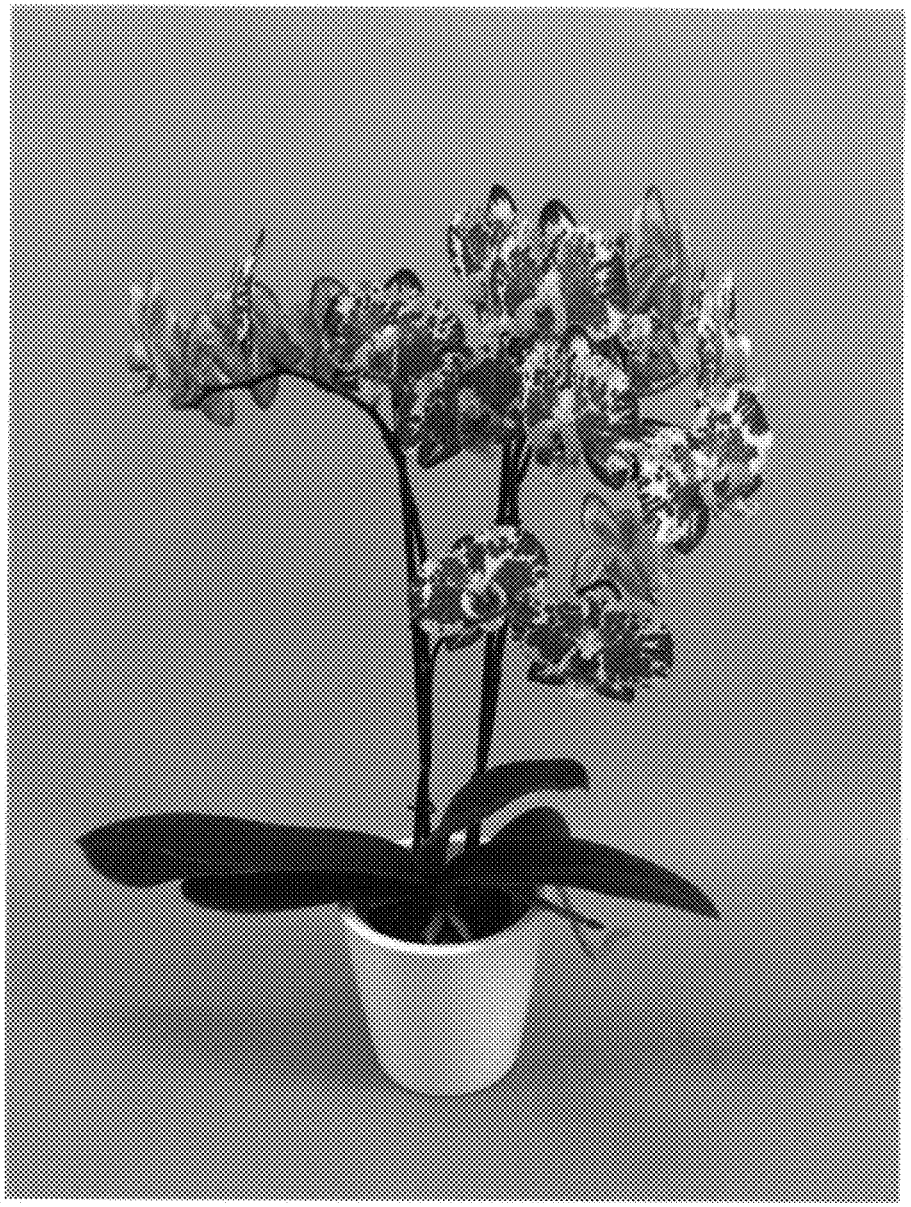
FIG. 1 shows the overall plant habit, including blooms and foliage of 'PHALGULFQ'.
Figure 2:
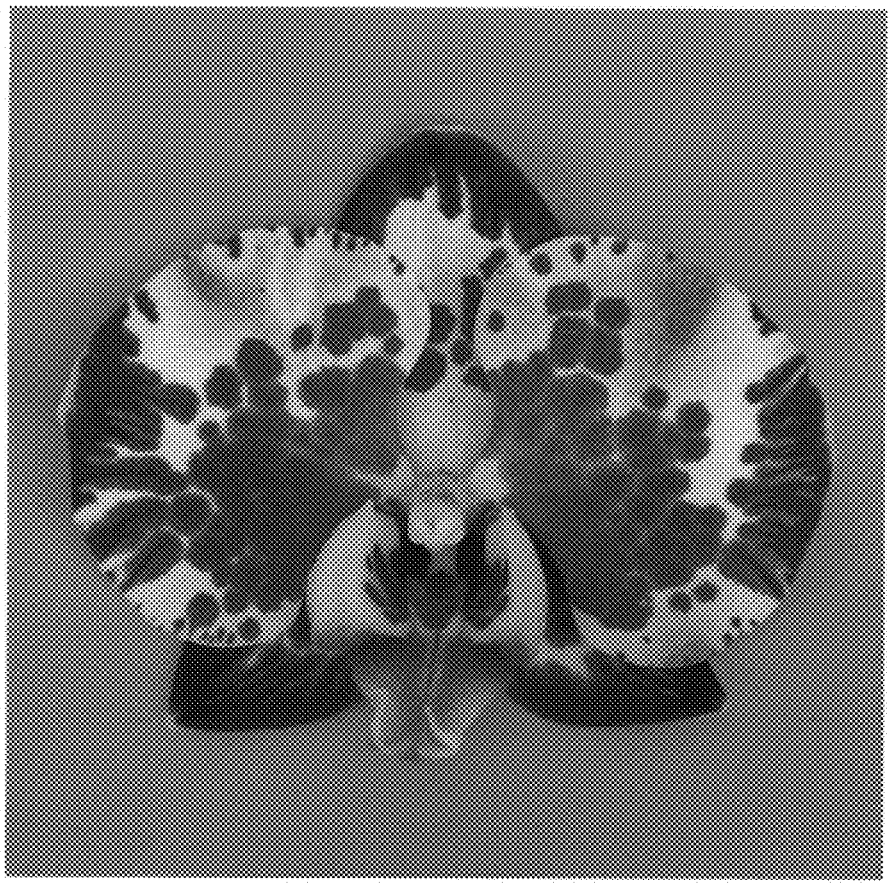
FIG. 2 shows a close-up of a flower of 'PHALGULFQ'.
Figure 3:
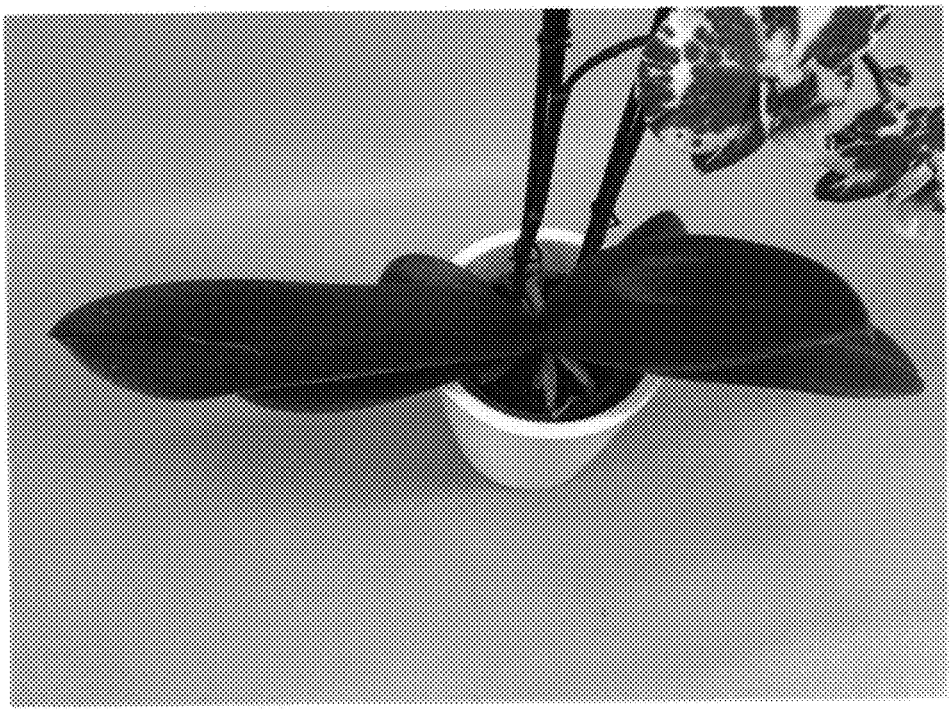
FIG. 3 shows a close-up of the leaves of 'PHALGULFQ'.

The following detailed description sets forth the distinctive characteristics of 'PHALGULFQ'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in July 2017 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGULFQ'.

Parentage:

*Female parent*.—*Phalaenopsis* cultivar '01-6226' (unpatented).

*Male parent*.—*Phalaenopsis* cultivar '01-6227' (unpatented).

Propagation:

*Type*.—Meristem tissue culture.

Roots:

*Root description*.—Greyed-green colored roots (RHS 190B/C) with branching lateral roots having brown colored root tips (RHS 200C).

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height* (*from soil level to top of inflorescence*).—Approximately 45.0 cm to 55.0 cm.

*Width* (*measured from leaf tips*).—About 41.0 cm to 43.0 cm.

*Vigor*.—Moderate.

Leaves:

*Mature leaves*.—Quantity per plant: 6 to 8 leaves are produced before flowering. Length (fully expanded): 21.0 cm to 23.0 cm. Width: 7.5 cm to 8.5 cm. Shape: Oblong. Base shape: Moderately elongated to elongated. Apex: Obtuse unequal. Leaf blade angle with the petiole (measured from the horizontal position): Between 20 degrees and 30 degrees. Leaf margin: Entire. Color: Upper surface: RHS 147A. Lower surface: RHS 147B. Texture: Rough. Thickness: 2.4 mm to 2.7 mm. Venation: Pattern: Parallel. Color of the midvein: Upper surface: RHS 147A. Lower surface: RHS 146B.

Peduncle:

*Quantity per plant*.—1 to 3.

*Number of flowers per peduncle*.—11 to 16.

*Length*.—45.0 cm to 55.0 cm.

*Diameter*.—6.0 mm to 6.5 mm.

*Strength*.—Strong.

*Aspect*.—Upright to slightly pendant.

*Texture*.—Smooth.

*Color*.—Brown (RHS 200A) with a touch of green (RHS 147B).

*Internode length*.—5.0 cm to 6.0 cm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 240.0 mm to 270.0 mm.

*Flowering time*.—First flowers can be expected 10 to 11 months after planting in a 12 cm (diameter) pot.

*Flower*.—Height: 75.0 mm to 80.0 mm. Diameter: 88.0 mm to 93.0 mm. Depth of lip: 26.0 mm to 28.0 mm.

*Flower longevity*.—On the plant: 10 to 16 weeks.

*Fragrance*.—Absent.

*Flower bud*.—Average size: Large. Length: 21.0 mm to 23.0 mm. Width: 19.0 mm to 21.0 mm. Shape: Egg shaped. Color: Green (RHS 146D) and diluting red-purple flecks (RHS N79A and N79C).

*Petals*.—Arrangement: Open/free. Shape: Semi-circular. Apex: Obtuse asymmetric. Margin: Slightly undulated. Length (from base to tip): 41.0 mm to 43.0 mm. Width: 54.0 mm to 56.0 mm. Color (when fully opened): Upper surface: Basic color: White (RHS NN155C). Over color: Light purple (RHS 76A); red-purple flecks (N78A) and purple-red edge (RHS N79C). Lower surface: Basic color: White (RHS NN155C). Over color: Light purple (RHS 76B) and light red-purple (RHS N78B/C) region toward the edge.

*Dorsal sepal*.—Shape: Elliptic. Apex: Obtuse symmetric. Margin: Entire. Length (from base to tip): 42.0 mm to 44.0 mm. Width: 27.0 mm to 29.0 mm. Color (when fully opened): Upper surface: Basic color: White (RHS NN155C). Over color: Red-purple flecks (RHS N78A) and purple-red edge (RHS N79C and 187B). Lower surface: Basic color: White (RHS NN155C). Over color: Light purple blush (RHS N78C).

*Lateral sepals*.—Shape: Ovate. Apex: Obtuse asymmetric. Margin: Entire. Length (from base to tip): 43.0 mm to 45.0 mm. Width: 25.0 mm to 27.0 mm. Color (when fully opened): Upper surface: Basic color: White (RHS NN155C). Over color: Red-purple flecks (RHS N78C) and purple-red edge (RHS N78A and N79C). Lower surface: Basic color: White (RHS NN155C). Over color: Light purple (RHS N78C) and light green (RHS 145C); and purple-red edge (RHS N79C).

*Labellum* (*lip*).—Whiskers: Present. Length of whiskers: 11.0 mm to 13.0 mm. Color of whiskers: Light purple (RHS 76D). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated. Length: 20.0 mm to 22.0 mm. Width: 17.0 mm to 19.0 mm. Color: White (RHS NN155C); yellow (RHS 12A) and on one side brown (RHS 175C), light purple (RHS 76B) on the other side; red-brown stripes (RHS 183C) at the base.

*Apical lobe*.—Shape: Triangular. Margin: Entire. Length: 19.0 mm to 21.0 mm. Width: 20.0 mm to 22.0 mm. Color: Light purple (RHS N78D); red at the base (RHS 185A) with yellow stripe (RHS 11A) in the middle; light purple shade (RHS N78B) toward whiskers.

*Callus*.—Average size: Large. Height: 7.0 mm to 8.0 mm. Length: 6.0 mm to 8.0 mm. Width: 4.0 mm to 5.0 mm. Color: Light brown (RHS 175B) and light yellow (RHS 8D) on sides.

Reproductive organs:

*Column*.—Length: 10.0 mm to 12.0 mm. Diameter: 6.0 mm to 7.0 mm. Color: White (RHS NN155C) with light purple shade (RHS 76A/B).

*Pollinia*.—Quantity: 2. Diameter: 1.5 mm to 1.7 mm. Color: Orange-yellow (RHS 17A).

*Ovary*.—Length: 12.0 mm to 14.0 mm. Diameter: 2.6 mm to 2.8 mm.

*Pedicel*.—Length: 43.0 mm to 45.0 mm. Diameter: 3.2 mm to 3.4 mm. Color: Green at the base (RHS 146C); light green (RHS 145D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

The female and male parent plants of 'PHALGULFQ' are no longer in existence, so a meaningful comparison cannot be made.

'PHALGULFQ' is most similar to the commercial *Phalaenopsis* plants named 'PHALDUZAH' (U.S. Plant Pat. No. 26,830) and 'PHALDOPFO' (U.S. Plant Pat. No. 29,452). 'PHALGULFQ' differs from the commercial variety 'PHALDUZAH' in that 'PHALGULFQ' has flowers with a flecked and edged pattern, an obtuse asymmetric petal apex and a light brown callus, whereas 'PHALDUZAH' has flowers with a flecked pattern, an emarginated petal apex and a dark red callus. Additionally, 'PHALGULFQ' has shorter whiskers than 'PHALDUZAH'.

'PHALGULFQ' differs from the commercial variety 'PHALDOPFO' in that 'PHALGULFQ' has an obtuse asymmetric petal apex and a light brown callus, whereas 'PHALDOPFO' has a rounded petal apex and a yellow, dotted callus. Additionally, 'PHALGULFQ' has smaller flowers and shorter whiskers than 'PHALDOPFO'.

I claim:

1. A new and distinct variety of *Phalaenopsis* plant named 'PHALGULFQ', substantially as described and illustrated herein.

* * * * *